United States Patent [19]

Wells et al.

[11] Patent Number: 4,765,899

[45] Date of Patent: Aug. 23, 1988

[54] APPARATUS FOR CONTINUOUS SEPARATION OF LEUKOCYTE/PLATELET-ENRICHED FRACTION FROM WHOLE BLOOD

[75] Inventors: John R. Wells, Culver City, Calif.; John W. Grant, Blacksburg, Va.

[73] Assignee: E. I. Du Pont de Nemours and Company, Wilmington, Del.

[21] Appl. No.: 897,360

[22] Filed: Aug. 18, 1986

Related U.S. Application Data

[63] Continuation of Ser. No. 540,773, Oct. 11, 1983, Pat. No. 4,663,058.

[51] Int. Cl.⁴ ............................................. B01D 21/00
[52] U.S. Cl. ................................. 210/519; 210/521; 422/44

[58] Field of Search .............. 210/801, 802, 521, 522, 210/519, 928; 422/44; 494/67–70, 73; 436/63, 174

[56] References Cited

U.S. PATENT DOCUMENTS

| | | |
|---|---|---|
| 2,728,457 | 12/1955 | Clarke .................................. 210/801 |
| 3,225,936 | 12/1965 | Ballestra .............................. 210/519 |
| 4,067,813 | 1/1978 | Pielkenrood ........................ 210/322 |
| 4,409,106 | 10/1983 | Furuta et al. ........................ 210/800 |
| 4,424,132 | 1/1984 | Iriguchi ................................ 210/800 |

Primary Examiner—Benoit Castel

[57] ABSTRACT

Continuous, noncentrifugal, unit gravity, sedimentation apparatus for separating blood into an erythrocyte-enriched plasma fraction and a leukocyte/platelet-enriched plasma fraction.

6 Claims, 2 Drawing Sheets

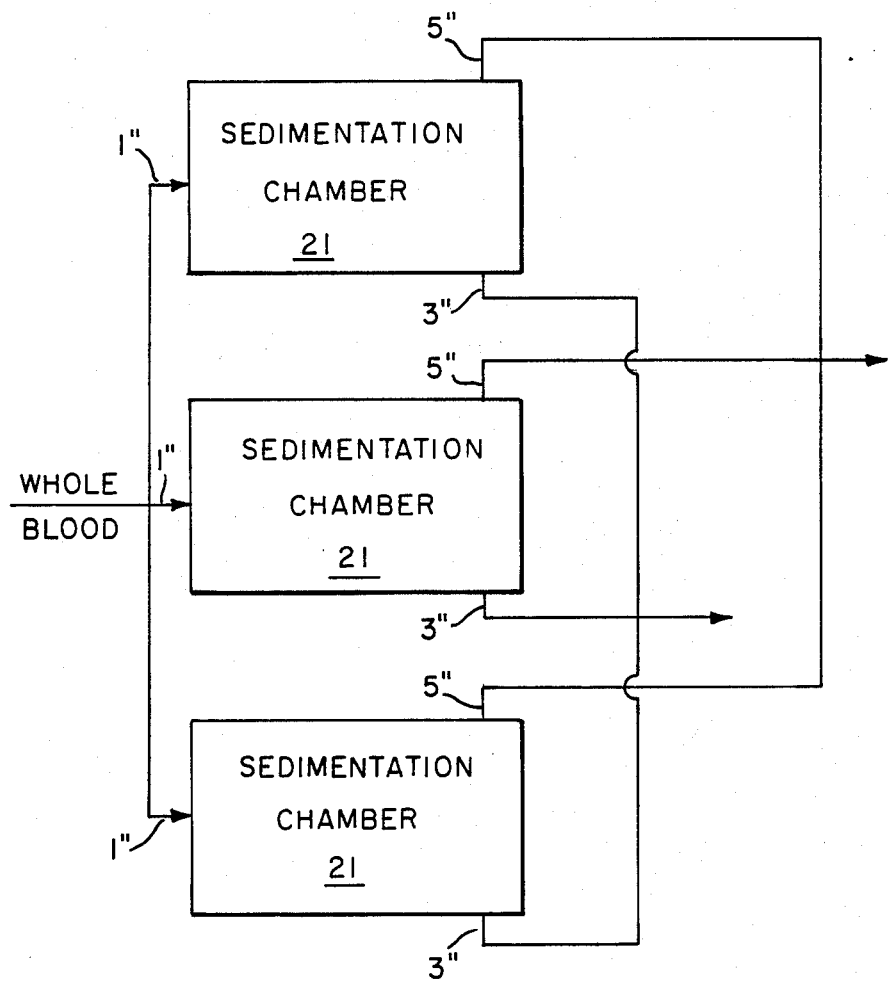

APPARATUS FOR CONTINUOUS SEPARATION OF LEUKOCYTE/PLATELET-ENRICHED FRACTION FROM WHOLE BLOOD

This is a continuation of application Ser. No. 540,773, filed Oct. 11, 1983 and issued May 5, 1987 as U.S. Pat. No. 4,663,058.

FIELD OF THE INVENTION

This invention relates to an apparatus for continuously separating whole blood into an erythrocyte-enriched plasma fraction and a leukocyte/platelet-enriched plasma fraction.

BACKGROUND INFORMATION

Extracorporeal processing of blood, either to remove certain disease-contributing constituents or to obtain specific fractions for subsequent therapeutic use, is becoming increasingly important in medicine. The term "pheresis" generally is applied to procedures involving the removal of blood from a donor or patient, separation of certain constituents from the removed blood, and subsequent return of the remaining blood constituents, including erythrocytes (red blood cells), to the donor or patient. Separation of plasma or plasma constituents from blood is known as "plasmapheresis"; separation of platelets, as "plateletpheresis"; and separation of leukocytes (white blood cells), as "leukapheresis". Although platelets or leukocytes can be removed separately, in many instances both are collected simultaneously for subsequent use in treatment (transfusion) of cancer patients whose blood-clotting and infection-fighting abilities have both been seriously compromised, either by the disease itself or by therapeutic procedures used to treat it.

Currently, most pheresis procedures involving removal of cellular constitutents are performed using continuous, semi-continuous or batchwise centrifugation. However, so-called "filtration leukapheresis" procedures have also been used to selectively remove certain white blood cell types from blood using a suitable sorbent, for example, as in the collection of granulocytes from blood by passing the blood over a suitable nylon-containing filter bed. U.S. Pat. No. 4,111,199 discloses a batchwise process for collection of leukocytes, the process comprising centrifuging whole blood to separate erythrocytes and leukocytes from supernatant plasma and platelets, resuspending the sedimented erythrocyte/leukocyte mixture in a saline solution containing an agent which selectively increases the sedimentation rate of erythrocytes by causing their aggregation, and then allowing the erythrocytes to separate at unit gravity from a supernatant containing nonsedimented leukocytes. The sedimentation of erythrocytes, with and without use of sediment-enhancing agents, is discussed by Cutts in "Cell Separation," Academic Press (1970), pp. 35-69, and continuous flow separators are discussed in "Leukocytes: Separation Collection and Transfusion," edited by Goldman and Lowenthal, Academic Press (1975), pp. 3-13 and 30-42.

It is an object of this invention to provide a continuous, noncentrifugal apparatus for efficiently separating whole blood, at unit gravity, into an erythrocyte-enriched plasma fraction and a leukocyte/platelet-enriched plasma fraction. Further separation of components of the leukocyte/platelet-enriched fraction can then be effected, if desired, by means which will be described hereinafter. Another object is to provide a continuous noncentrifugal apparatus which is efficient for collection of a leukocyte/platelet fraction containing minimal levels of erythrocytes so that significant depletion of a patient's or donor's erythrocyte level does not result from repeated phereses procedures to obtain leukocytes. Still another object is to provide such an apparatus which is mechanically simple, easy to fabricate and use, and provides a virtually enclosed system. Other objects will become apparent hereinafter.

BRIEF DESCRIPTION OF THE DRAWINGS

FIG. 3 depicts a flow chart showing three blood sedimentation apparatus of the invention in parallel assemblage.

DISCLOSURE OF THE INVENTION

Figure 1:
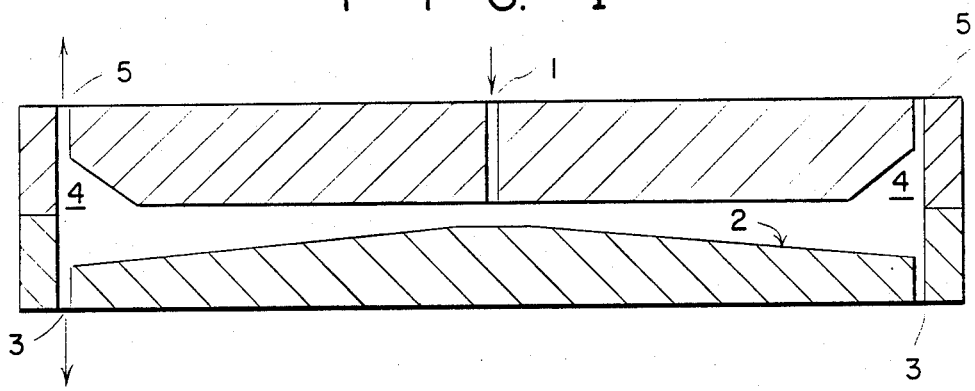
FIG. 1 depicts a section view of the blood sedimentation chamber which has a circular chamber floor and which was used in Example 1.

For further comprehension of the invention, and of the objects and advantages thereof, reference may be made to the following description and accompanying drawings, and to the appended claims in which the various novel features of the invention are more particularly set forth.

The invention resides in the discovery of a continuous, noncentrifugal, unit gravity sedimentation process for whole blood. By "continuous unit gravity sedimentation" is meant sedimentation at unit gravity under continuous flow conditions. "Whole blood" means blood containing erythrocytes, leukocytes and platelets in plasma. More particularly, the invention resides in a process for separating whole blood into an erythrocyte-enriched plasma fraction and a leukocyte/platelet-enriched plasma fraction, which process comprises continuously flowing the blood, at unit gravity, in a confined flow path, to form an interface 15 (FIG. 2) which separates a leukocyte/platelet-enriched plasma upper layer and an erythrocyte-enriched plasma lower layer, and thereafter continuously removing leukocyte/platelet-enriched plasma from the upper layer and erythrocyte-enriched plasma from the lower layer. In a preferred embodiment, the flow path is declined from beginning to end and a sediment-enhancing agent is added to the blood to facilitiate formation of red blood cell aggregates, thereby enhancing the rate of their sedimentation relative to that of leukocytes and platelets. "Red blood cell aggregate" means a reversible physical association ("rouleaux formation") of erythocytes. Sediment-enhancing agents are well known and are described, for example, by Cutts, supra. Known agents include fibrinogen, dextran, phytohemagglutinin, polyvinylpyrrolidone, gelatin, gum acacia, globulin, pectins, quaternary ammonium salts, Plasmagel, Ficoll ® and hydroxyethyl starch (HES). One skilled in the art will appreciate that selection of a particular agent involves consideration of the purpose for which blood is being fractionated. For example, HES is commonly used in centrifugal leukapheresis procedures involving return of the added sedimenting agent to the patient or donor along with the reinfused blood fractions. In the instant invention, when HES is used, the blood is preferably treated, in a 3:1 to 7:1 ratio, with 3 to 6% HES solution (that is, 3 to 7 parts of blood to one part, by volume, of HES).

In the process of the invention blood is conducted into a sedimentation chamber which includes at least one inlet, at least two outlets and a chamber floor across which the blood flows in a confined flow path from inlet to outlets. The outlets consist of at least one outlet for the erythrocyte-enriched plasma fraction and at least one outlet for the leukocyte/platelet-enriched plasma fraction. Preferably, the chamber floor increases in area from the inlet to the outlets. Also, preferably, the chamber floor is declined, that is, the base of the floor near the blood inlet is raised relative to the base of the floor near the outlet(s) for the erythrocyte-enriched plasma fraction. The blood flow path is thus declined. More specifically, the outlet(s) for the leukocyte/platelet-enriched plasma fraction is above a horizontal plane which includes the highest point of the blood inlet, and the outlet(s) for the erythrocyte-enriched plasma fraction is below a horizontal plane which includes the lowest point of the blood inlet. After the length of the chamber floor is suitably selected, the flow rate of the blood is regulated so that a clear interface between the lower erythrocyte-enriched plasma fraction and the upper leukocyte/platelet-enriched plasma fraction is formed near the end of the blood flow path, that is, near the outlets. This can be referred to as the "operating point". The position of the interface can be determined optically, for example, visually, but it preferably is determined by known electronically controlled optics, for example, using a photocell. The flow rate should be slow enough that any red blood cell aggregates which have separated are not resuspended, for example, as a result of turbulence, hydraulic jumps or local fluid disturbances which create convective mixing. Stated in another way, the flow should be laminar, as opposed to turbulent, and should exhibit a Reynolds number of less than 2000. The Froude's number, which is the ratio of inertial force to gravitational force, should be less than one, indicative of subcritical flow. A Froude's number of greater than one is indicative of supercritical flow. It is to be understood that selection of the optimum operating conditions (operating point) will depend on blood hematocrit, flow rate, sedimentation rate and height of the sedimentation path. Blood flow rate can be controlled by means known in the art, for example, by a simple clamping arrangement, such as on the leukocyte line, or by electronic control means. Typically, the length of the flow, path is about 2.5 to 5 inches (63.5 to 127 mm) and the depth of the blood is up to about 30 mm. The volume of the sedimentation chamber is, preferably, about 100 to 200 mL. The chamber floor (and thus the blood flow path) is preferably declined so that the red blood cell aggregates which are formed migrate radially and sediment vertically without undue mixing. The angle of decline is greater than 0° but less than 90°; preferably, it is less than 30°; more preferably, it is about 4° to 10°. The "angle of decline" is the acute angle formed by the intersection of the chamber floor and an imaginary horizontal plane.

Anticoagulated whole blood, after addition of the sedimenting agent, is conducted into the sedimentation chamber in which erythrocytes migrate downward in response to gravity. Sedimentation of the erythrocytes results in an upward displacement of plasma-carrying leukocytes and platelets to form a leukocyte platelet-enriched layer which forms at the top of the blood flowing across the chamber floor, becoming clearly defined at the downstream end of the flow path, near the outlets. If desired, using centrifugation, filtration through a membrane of selected pore size, or adsorption/desorption procedures, the upper layer can be further separated. For example, specific types of leukocytes can be removed by passing the leukocyte/platelet plasma fraction over an insoluble support containing an immobilized species, such as a specific antibody which interacts with selected cell types.

Separating erythrocytes from blood to obtain a leukocyte/platelet-enriched plasma fraction by the process of the invention is efficient, can be maintained sterile, is mechanically simple, and requires a low extracorporeal blood volume, which is important if the procedure is carried out with the apparatus being connected to a patient or donor.

The invention also resides in a blood sedimentation apparatus comprising a chamber having a floor; at one end of the floor, an inlet for introduction of blood; and at the other end of the floor, the downstream end, a first outlet(s), appropriately positioned above the chamber floor, for removal of a leukocyte/platelet-enriched plasma fraction from the upper layer, and a second outlet(s), appropriately positioned in the base of the chamber floor, for removal of an erythrocyte-enriched plasma fraction from the lower layer. The sedimentation chamber is of rigid or semi-rigid construction and can be fabricated from any well-known blood-compatible material. Additional details regarding the chamber have been provided hereinabove.

As will be apparent to one skilled in the art, two or more of the blood sedimentation apparatus of the invention may be arranged in a parallel assemblage.

FIG. 3 is a flow chart showing three blood sedimentation apparatus of the invention in parallel assemblage. Whole blood enters each blood sedimentation chamber 21 through appropriate feed lines at 1". The erythrocyte plasma fraction is removed through outlet 3" of each chamber 21 and collected by passing through appropriate collection lines. The leukocyte/platelet-enriched plasma fraction is removed through outlet 5" of each chamber 21 and collected by passing through appropriate collection lines.

Referring to FIG. 1 which is illustrative of a preferred embodiment of the invention, whole blood enters a circular sedimentation chamber through inlet port 1, 0.13 inch (3.18 mm) in diameter, and flows, in a confined flow path, across chamber floor 2. The angle of decline of the chamber floor in this embodiment is 5° and the floor has a length of 3.63 inches (92.08 mm), this length being the radius of the circular floor. In the embodiment of FIG. 1 the depth of the flow path increases from inlet to outlets, it being understood that this increase in depth is not necessary to the invention. The erythrocyte plasma fraction is removed through outlet 3, 0.13 inch (3.18 mm) in diameter, eight of which are equidistantly spaced around the periphery of the chamber. The leukocyte/platelet-enriched plasma fraction is collected in channel 4 which is at the end of the chamber floor, and is removed through outlet port 5, 0.13 inch (3.18 mm) in diameter, eight of which are equidistantly spaced around the periphery of the chamber. In this circular sedimentation chamber, the depth of channel 4 is 20 mm. The total volume of the chamber is 280 mL. Although eight outlets 3 and eight outlets 5 have been used in this embodiment, any suitable number can be used.

Figure 2:
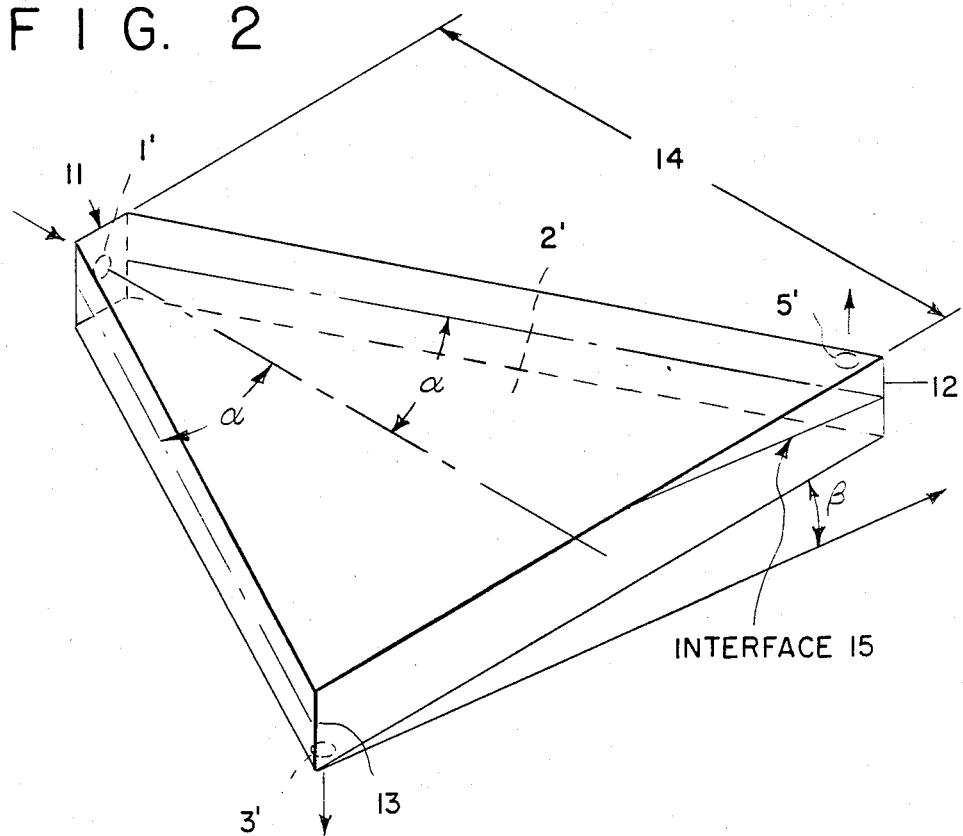
FIG. 2 depicts an elevation view of the blood sedimentation chamber which has a wedge-shape chamber floor and which was used in Example 2.

Referring to FIG. 2 which is illustrative of a wedge-shaped sedimentation chamber having a wedge-shaped chamber floor 2', blood enters inlet port 1' at apex 11 and flows, in a confined flow path, at a constant depth in this embodiment, in an increasing volume, as the area of the chamber floor increases, towards the opposite end of the chamber, it being understood that this increase in area is not necessary to the invention. The length of the chamber, line 14, is 7.5 inches (190.5 mm) and the blood depth is 0.5 inch (12.7 mm), the total volume of the chamber being 30 mL. Angle α is 30°. The chamber is angled from a horizontal orientation such that apex 12 is raised from apex 13 by the angle of decline β which is 10°. The erythrocyte plasma fraction is removed from the lower layer through outlet 3' at the bottom of the chamber floor at apex 13, while the leukocyte/platelet-enriched plasma fraction is removed from the upper layer through outlet 5' at apex 12.

The following examples are illustrative of the process of the invention.

EXAMPLE 1

In the following table are listed the average conditions and results of three experiments carried out using the sedimentation chamber illustrated in FIG. 1. In all three experiments, human blood, which was collected using heparin as anticoagulant and subsequently diluted 7:1 in 6% HES in anticoagulant-citrate-dextrose (ACD) solution, was used. The blood was recycled through the sedimentation chamber for about 15 to 20 minutes after which the erythrocyte and leukocyte/platelet plasma fractions were collected for about five minutes.

| | |
|---|---|
| Initial volume of anticoagulated whole blood with HES added | 366 mL |
| Initial leukocyte count (whole blood) | $6.2 \times 10^6$/mL |
| Inlet flow rate | 28 mL/min |
| Leukocyte/platelet plasma fraction outlet flow rate | 15 mL/min |
| Leukocyte count in upper plasma fraction | $8.5 \times 10^6$/mL |
| Leukocyte recovery rate in leukocyte/platelet fraction | 73.4% |

EXAMPLE 2

In three experiments carried out using the sedimentation chamber illustrated in FIG. 2 with human blood collected in heparin and diluted 6:1 in 6% HES in ACD, the inlet flow rate was 4.6 mL/min and the leukocyte/platelet plasma fraction outlet flow rate was 2.0 mL/min. The leukocyte recovery rates were 81%, 79% and 77%, respectively.

Based on a series of runs using the process of the invention in the apparatus of the invention, hematocrits (volume percent of erythrocytes) of less than 1% have been achieved routinely for the leukocyte/platelet plasma fraction.

BEST MODE FOR CARRYING OUT THE INVENTION

The best mode presently contemplated for carrying out the invention resides in the embodiment of FIG. 1 and Example 1.

Industrial Applicability

The medical significance of separating blood into an erythrocyte-enriched plasma fraction and a leukocyte/platelet-enriched plasma fraction is well known in the art, as is the further processing of the latter plasma fraction to separate platelets, leukocytes, or specific types of leukocytes. The present invention provides ready means for carrying out the above operations.

While the preferred embodiments of the invention are illustrated and described by the above, it is to be understood that the invention is not limited to the precise constructions herein disclosed and that the right to all changes and modifications coming within the scope of the invention as defined in the following claims is reserved.

We claim:

1. Improved, continuous, noncentrifugal, whole blood sedimentation apparatus, said apparatus providing improved sedimentation efficiency and comprising a chamber having a floor; at one end of the floor, an inlet means for introduction of blood; and at the other end of the floor, a first outlet means, above the floor, for removal of an erythrocyte-depleted, leukocyte/platelet-enriched plasma fraction, and a second outlet means, in the base of the floor, for removal of an erythrocyte-enriched plasma fraction, said floor being declined from said inlet means to said second outlet means at an angle greater than 0° but less than 30°, and wherein the area of the floor increases from said inlet means to said second outlet means.

2. Apparatus of claim 10 wherein the floor is declined so that the angle of decline is about 4° to 10°.

3. Apparatus of claim 1 wherein the chamber and the floor are circular, the inlet means is at the center of the circular floor, and the first and second outlet means are positioned around the periphery of the circular chamber.

4. Apparatus of claim 3 wherein the radius of the circular floor is 2.5 to 5 inches (63.5 to 127 mm).

5. Apparatus of claim 3 wherein the first and second outlet means each comprise a plurality of openings equidistantly spaced around the periphery of the chamber.

6. System comprising a plurality of blood sedimentation apparatus arranged in parallel, each sedimentation apparatus being defined by the apparatus of claim 1.

* * * * *